(12) United States Patent
Uchida et al.

(10) Patent No.: US 12,181,656 B2
(45) Date of Patent: Dec. 31, 2024

(54) ENDOSCOPE

(71) Applicant: OLYMPUS CORPORATION, Tokyo (JP)

(72) Inventors: Ramiya Uchida, Tachikawa (JP); Masanobu Koitabashi, Hachioji (JP); Yasuhiro Okamoto, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 874 days.

(21) Appl. No.: 17/215,739

(22) Filed: Mar. 29, 2021

(65) Prior Publication Data

US 2021/0212554 A1 Jul. 15, 2021

Related U.S. Application Data

(63) Continuation of application No. PCT/JP2018/036700, filed on Oct. 1, 2018.

(51) Int. Cl.
*A61B 1/00* (2006.01)
*A61B 1/005* (2006.01)
*G02B 23/24* (2006.01)

(52) U.S. Cl.
CPC ...... *G02B 23/2476* (2013.01); *A61B 1/00032* (2013.01); *A61B 1/0004* (2022.02); *A61B 1/00042* (2022.02); *A61B 1/00066* (2013.01); *A61B 1/0052* (2013.01)

(58) Field of Classification Search
CPC ............ A61B 1/00042; A61B 1/00066; A61B 1/0016; A61B 1/0052
USPC .......................................................... 600/132
See application file for complete search history.

(56) References Cited

U.S. PATENT DOCUMENTS

| | | | | |
|---|---|---|---|---|
| 4,499,895 A | * | 2/1985 | Takayama | A61B 1/0052 600/149 |
| 2009/0076330 A1 | * | 3/2009 | Ashida | A61B 1/0052 600/146 |
| 2012/0302829 A1 | * | 11/2012 | Omoto | A61B 1/0052 600/109 |
| 2013/0060088 A1 | * | 3/2013 | Okamoto | A61B 1/0052 600/146 |
| 2013/0267775 A1 | * | 10/2013 | Okamoto | A61B 1/0016 600/109 |
| 2014/0012087 A1 | * | 1/2014 | Omoto | A61B 1/0052 600/146 |

(Continued)

FOREIGN PATENT DOCUMENTS

| | | |
|---|---|---|
| EP | 2 609 847 A1 | 7/2013 |
| EP | 2 820 999 A1 | 1/2015 |

(Continued)

OTHER PUBLICATIONS

International Search Report dated Dec. 18, 2018 received in PCT/JP2018/036700.

*Primary Examiner* — Aaron B Fairchild
(74) *Attorney, Agent, or Firm* — Scully, Scott, Murphy & Presser, P.C.

(57) ABSTRACT

An endoscope includes an insertion portion, an operation portion, a knob protruding from the operation portion to a first side in a direction intersecting a longitudinal direction, a universal cord protruding to a second side in the direction, and a power unit provided in a housing portion disposed on the operation portion on the second side so as not to stick out to the first side with respect to a center axis.

18 Claims, 7 Drawing Sheets

(56) References Cited

U.S. PATENT DOCUMENTS

2014/0135580 A1    5/2014  Omoto et al.
2017/0086651 A1*   3/2017  Sato .................... A61B 1/0052

FOREIGN PATENT DOCUMENTS

| | | |
|---|---|---|
| EP | 2 821 000 A1 | 1/2015 |
| JP | 2013129416 A | 7/2013 |
| JP | 5364868 B1 | 12/2013 |
| JP | 2014161644 A | 9/2014 |
| WO | 2012/074013 A1 | 6/2012 |
| WO | 2012/172953 A1 | 12/2012 |
| WO | 2013/129416 A1 | 9/2013 |
| WO | 2013/129494 A1 | 9/2013 |
| WO | 2014/065092 A1 | 5/2014 |
| WO | 2015/005095 A1 | 1/2015 |

\* cited by examiner

W2 > W1

ENDOSCOPE

CROSS-REFERENCE TO RELATED APPLICATION

This application is a continuation application of PCT/JP2018/036700 filed on Oct. 1, 2018, the entire contents of which are incorporated herein by this reference.

BACKGROUND OF THE INVENTION

1. Field of the Invention

The present invention relates to an endoscope including an insertion portion configured to be inserted into a subject or an object, and an operation portion provided on a proximal end side in a longitudinal direction of the insertion portion, and a power unit provided in the operation portion and configured to drive a mechanism for moving a specific part or another specific part of the insertion portion.

2. Description of the Related Art

In recent years, endoscopes have been widely used in medical fields and industrial fields. Endoscopes are capable of performing observation, treatment, and the like of a site to be examined in a subject or an object by inserting an elongated insertion portion into the subject or object.

In addition, an endoscope is known, which has a configuration in which a bending portion bendable in a plurality of directions, for example, is provided on a distal end side in a longitudinal direction (hereinafter, just referred to as distal end side) of an insertion portion of the endoscope.

The bending portion improves the advancing performance of the insertion portion at a flex portion in a tubular path, and also vanes an observation direction of an observation optical system provided in the distal end portion located on the distal end side with respect to the bending portion in the insertion portion.

The bending portion is configured to be bendable in any of four directions, i.e., up, down, left, and right directions, by the operator operating and rotating a knob provided on the operation portion of the endoscope. The knob is provided so as to protrude in one side in a direction intersecting the above-described longitudinal direction.

Specifically, when the knob is rotated, a pulley, which is provided in the operation portion and configured to rotate together with the knob, is rotated, to thereby cause a long member such as a chain, a wire, or the like, which is wound around the pulley and whose distal end in the longitudinal direction (hereinafter, just referred to as distal end) is fixed to the bending portion, to be pulled, and as a result, the bending portion is bent.

Note that the knob is rotated with the thumb of the left hand of the operator in the state where a grasping region of the operation portion is grasped with the palm, the little finger, the ring finger, and the middle finger of the left hand of the operator and a fixed portion side of a universal cord extended from the operation portion is grasped with the fixed portion side being held between the index finger and the thumb of the left hand of the operator.

When inserting the insertion portion of the endoscope into a subject or an object, the operator grasps the insertion portion with the right hand to perform operation for pushing the insertion portion into a deep part in the subject or object with the right hand, and grasps the operation portion with the left hand as described above to operate the above-described knob and various kinds of switches provided on the operation portion.

However, there has been a problem that it is difficult for an operator with small hands or an inexperienced operator to perform rotating operation of the knob for pulling the long member only with the thumb of the left hand as described above, since such rotating operation requires a large amount of operation force.

In view of such a problem, Japanese Patent No. 5364868 discloses a configuration in which an actuator as a power unit is provided in the operation portion so that pulling of the long member is electrically performed in order to reduce the amount of rotating operation force of the knob.

In the configuration disclosed in the Japanese Patent No. 5364868, a casing as a housing portion in which the actuator is housed is provided on the operation portion at a position between the knob and the universal cord in consideration of the weight balance of the operation portion at the time when an operator grasps the operation portion.

SUMMARY OF THE INVENTION

An endoscope according to one aspect of the present invention includes: an insertion portion configured to be inserted into a subject or an object; an operation portion provided on a proximal end side in a longitudinal direction of the insertion portion, and configured to operate the insertion portion; a knob protruding from the operation portion to a first side in a direction intersecting the longitudinal direction, the knob being configured to operate a specific part of the insertion portion; a cord provided so as to protrude to a second side in the direction intersecting the longitudinal direction, the second side being different from the first side to which the knob is protruded from the operation portion; and a power source provided in a housing member disposed on the operation portion on the second side and positioned so as not to stick out to the first side with respect to a center axis of the insertion portion, the power source being configured to drive a mechanism for moving the specific part or another specific part of the insertion portion.

DETAILED DESCRIPTION OF THE PREFERRED EMBODIMENT(S)

Hereinafter, an embodiment of the present invention will be described with reference to drawings.

Figure 1:
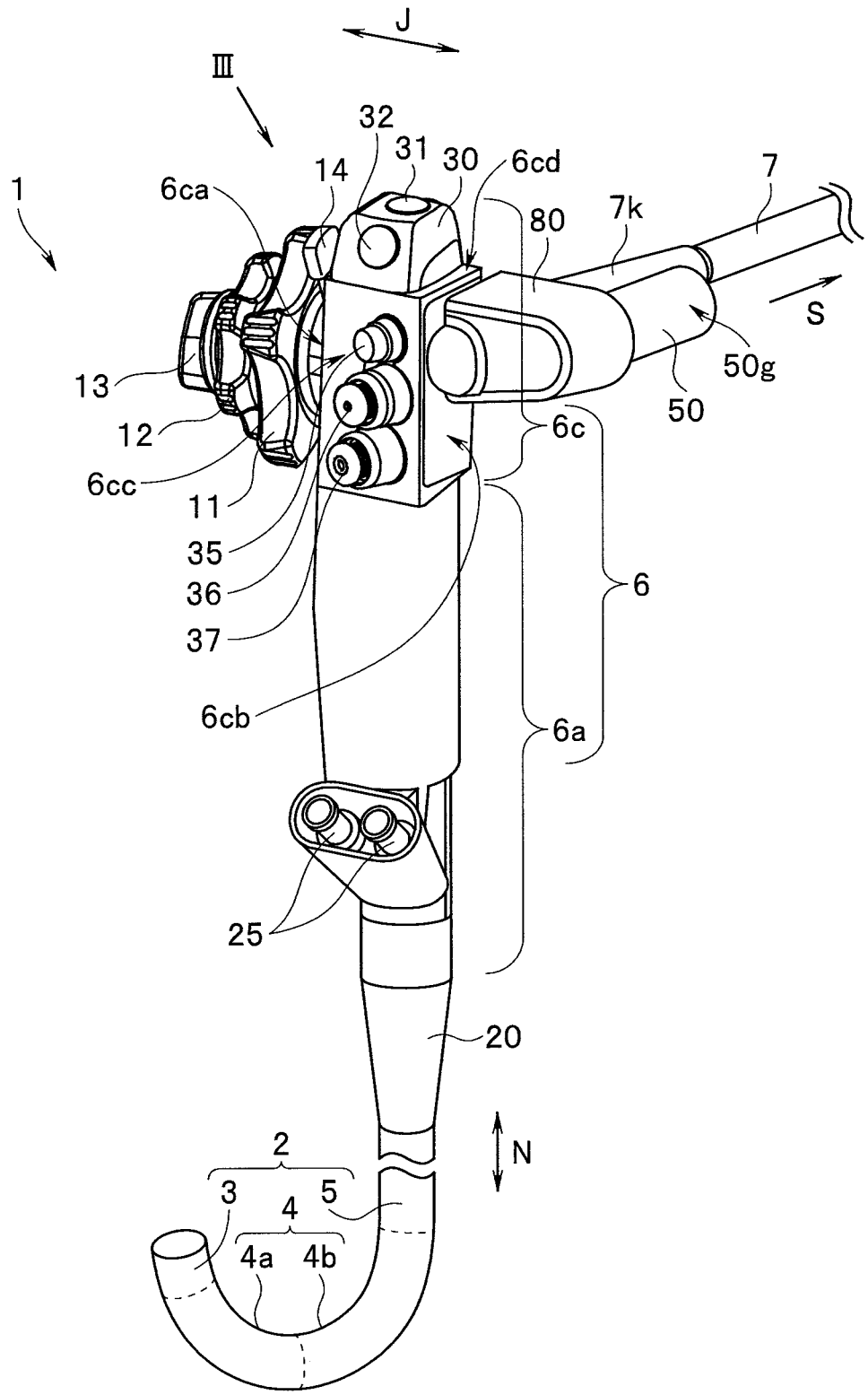
FIG. 1 is a partial perspective view illustrating an endoscope according to a present embodiment.
Figure 2:
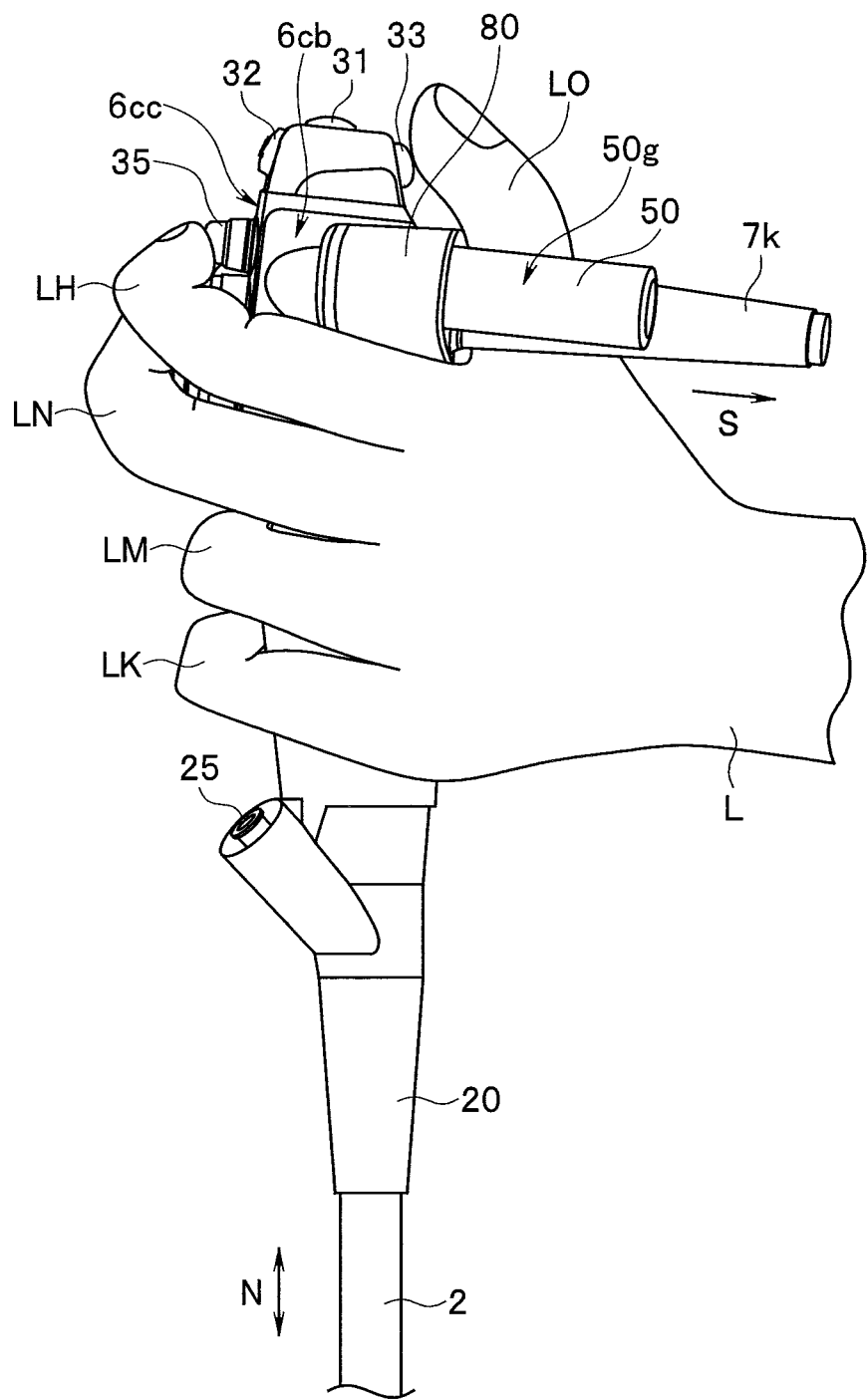
FIG. 2 illustrates a state where an operator grasps an operation portion of the endoscope in FIG. 1 with the left hand.

FIG. 1 is a partial perspective view illustrating an endoscope of the present embodiment. FIG. 2 illustrates a state where an operator grasps an operation portion of the endoscope in FIG. 1 with the left hand.

Figure 3:
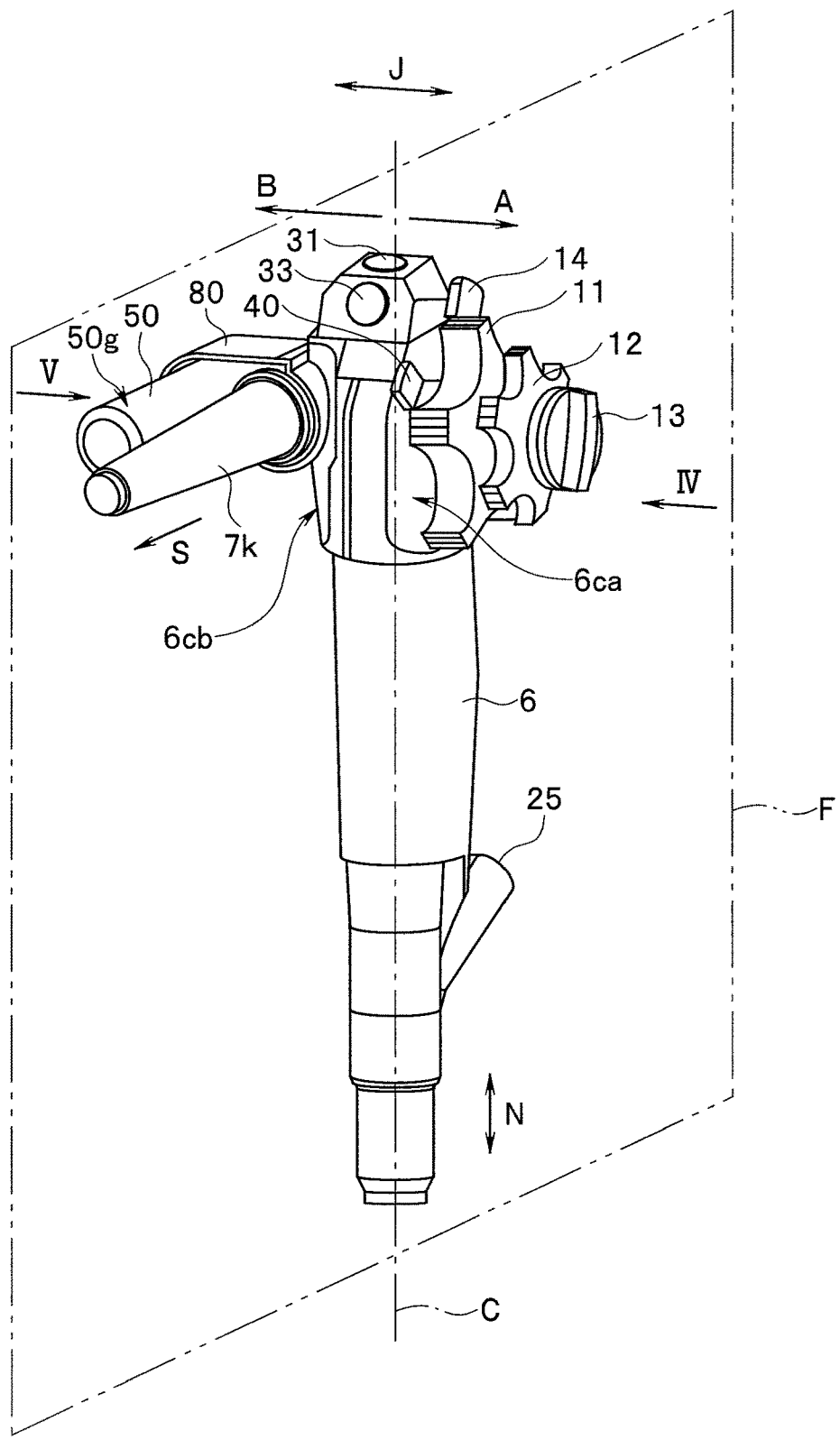
FIG. 3 is a perspective view of the operation portion, a universal cord fixing portion, a housing portion, and a break preventer of a universal cord of the endoscope in FIG. 1, when viewed from a direction of III in FIG. 1.
Figure 4:
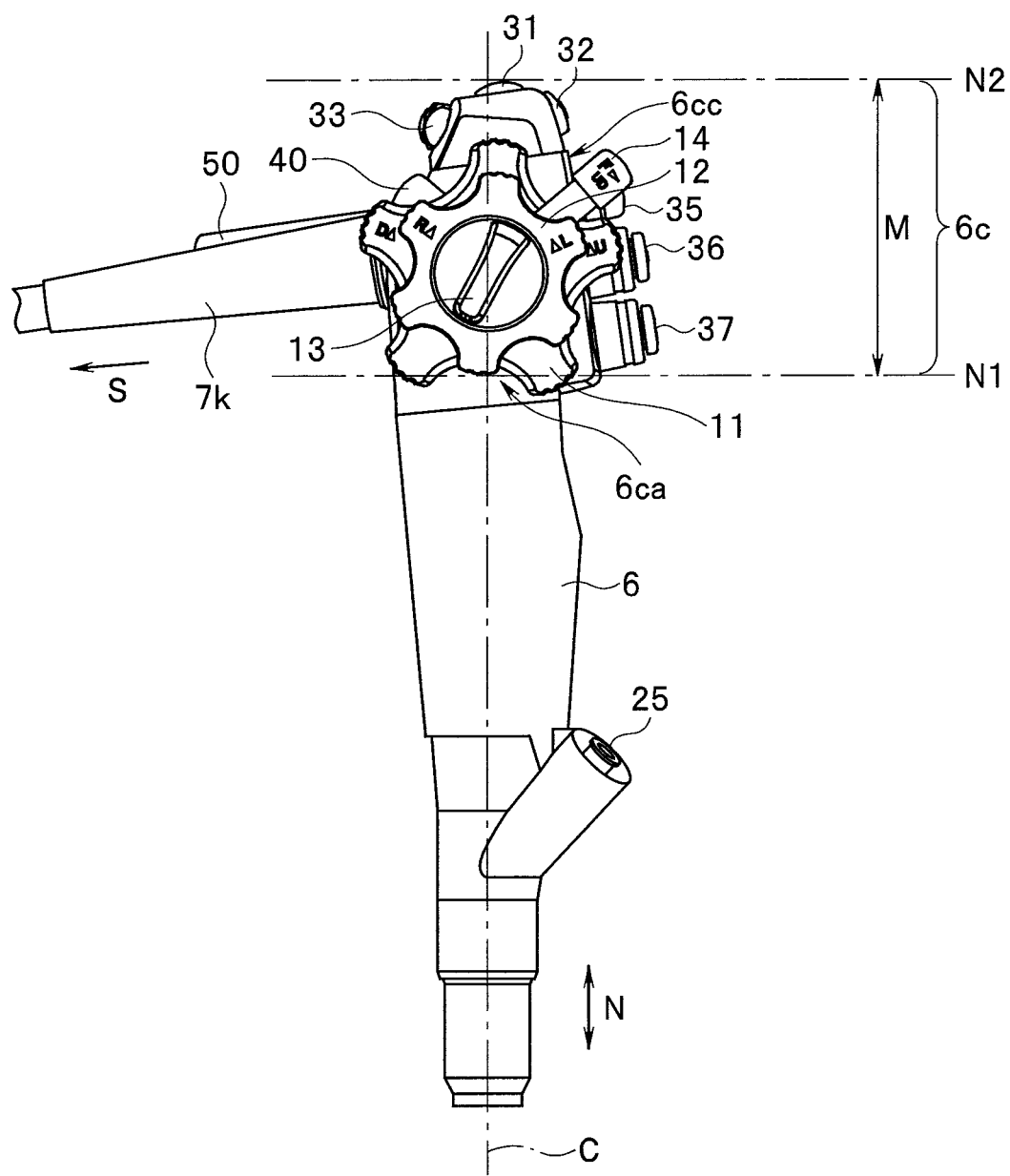
FIG. 4 is a plan view of the operation portion, the universal cord fixing portion, the housing portion, and the break preventer of the universal cord that are illustrated in FIG. 3, when viewed from a direction of IV in FIG. 3.

FIG. 3 is a perspective view of the operation portion, a universal cord fixing portion, a housing portion, and a break preventer of a universal cord of the endoscope in FIG. 1, when viewed from a direction of III in FIG. 1. FIG. 4 is a plan view of the operation portion, the universal cord fixing portion, the housing portion, and the break preventer of the universal cord that are illustrated in FIG. 3, when viewed from a direction of IV in FIG. 3.

Figure 5:
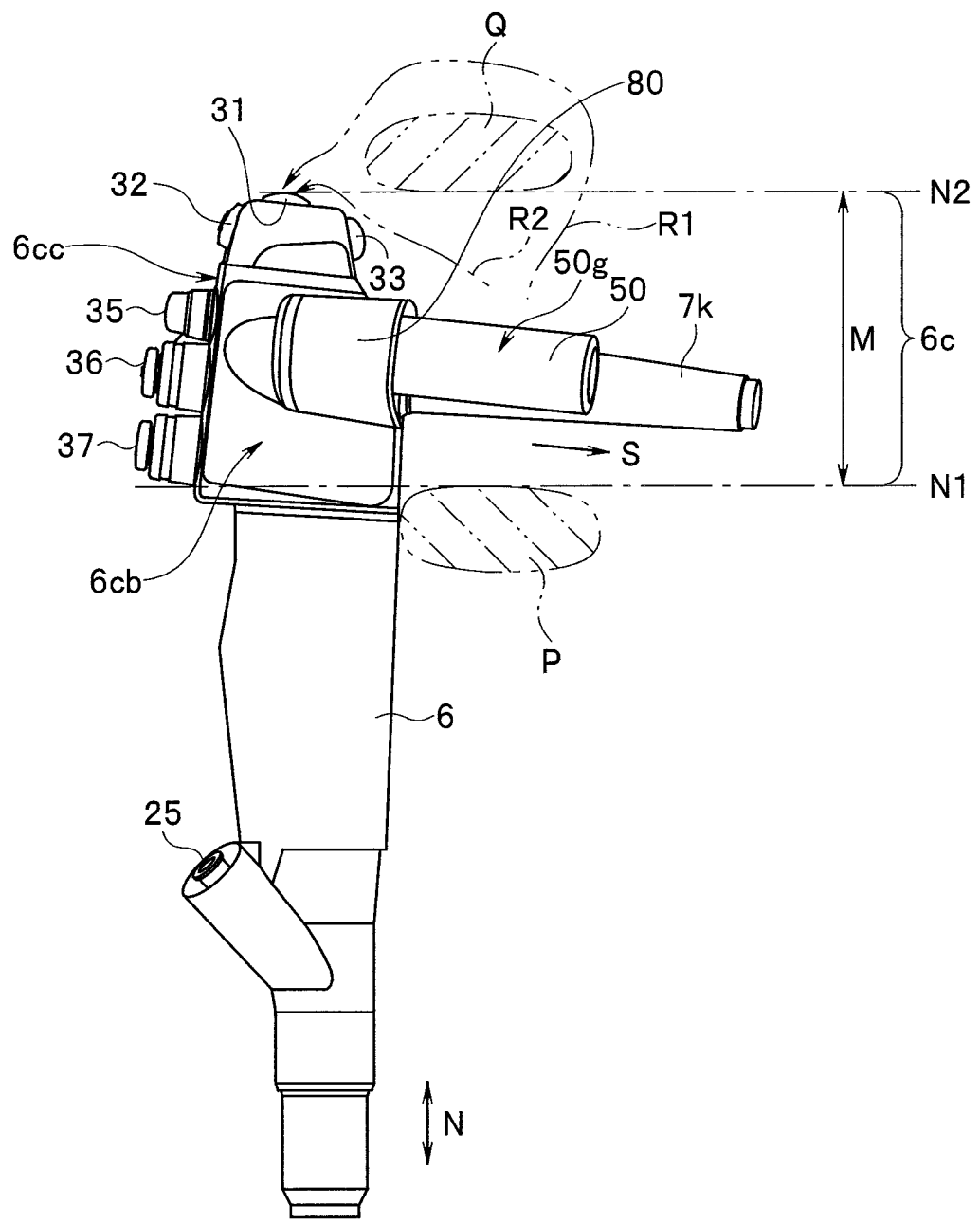
FIG. 5 is a plan view of the operation portion, the universal cord fixing portion, the housing portion, and the break preventer of the universal cord that are illustrated in FIG. 3, when viewed from a direction of V in FIG. 3.
Figure 6:
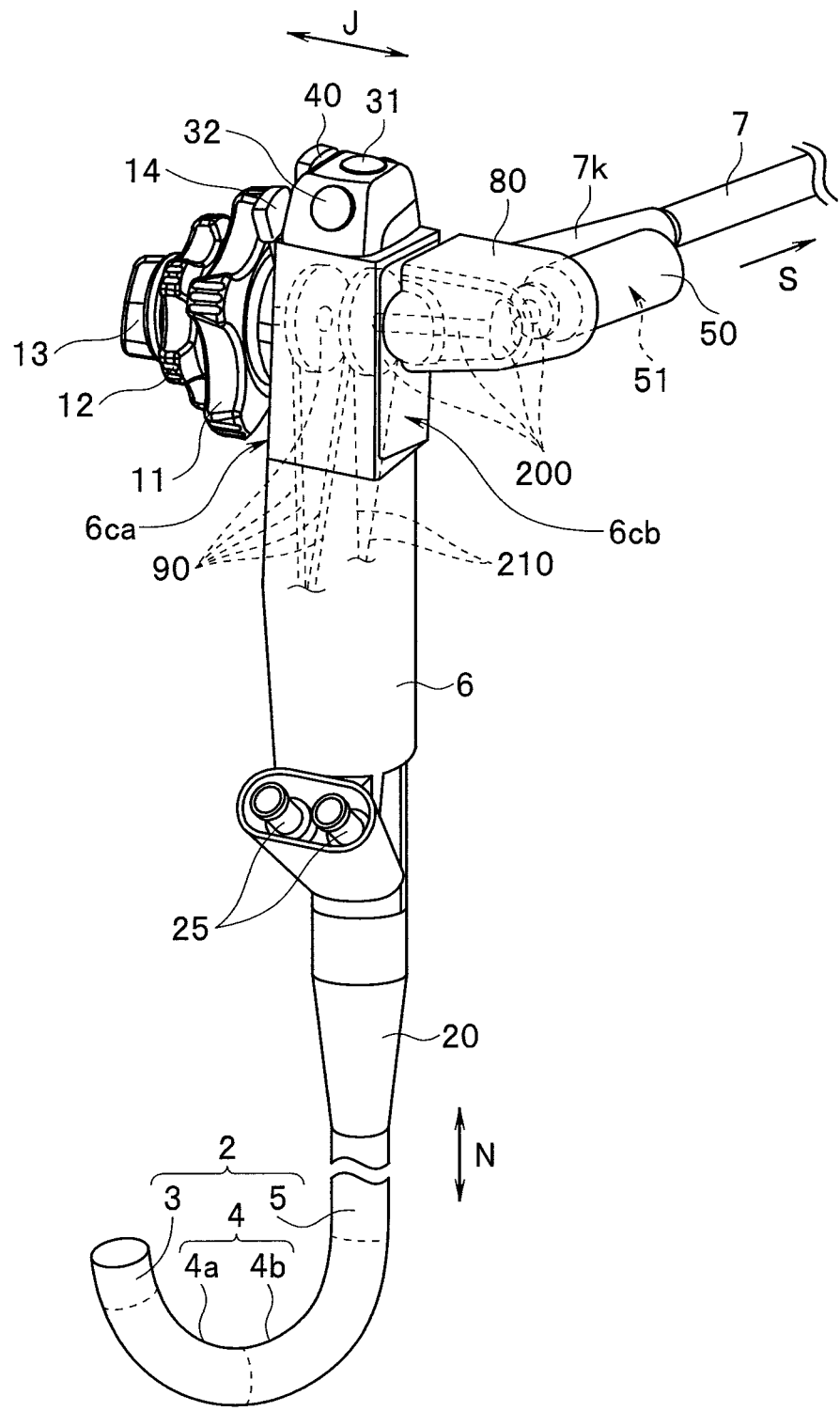
FIG. 6 is a perspective view of the endoscope, which schematically illustrates a configuration in which power of a power unit provided in the housing portion in FIG. 1 is transmitted to a power transmitting mechanism provided in the operation portion.

Furthermore, FIG. 5 is a plan view of the operation portion, the universal cord fixing portion, the housing portion, and the break preventer of the universal cord that are illustrated in FIG. 3, when viewed from a direction of V in FIG. 3. FIG. 6 is a perspective view of the endoscope, which schematically illustrates a configuration in which power of a power unit provided in the housing portion in FIG. 1 is transmitted to a power transmitting mechanism provided in the operation portion.

Figure 7:
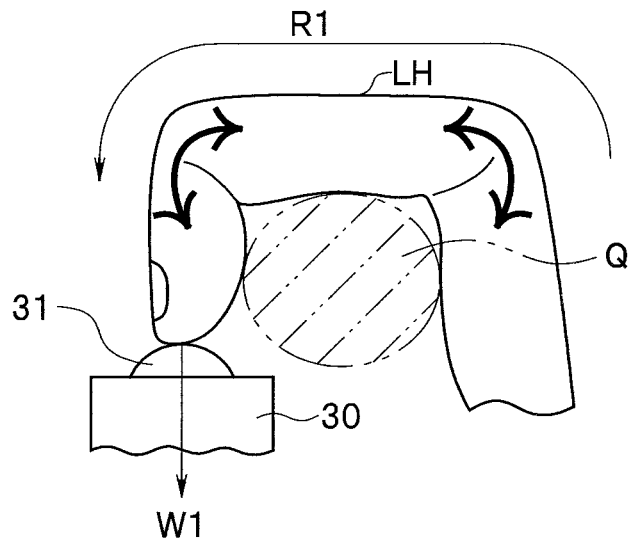
FIG. 7 schematically illustrates a situation where the operator who grasps the operation portion as illustrated in FIG. 2 depresses a switch button disposed at a top portion of a switch box in FIG. 2 with the index finger of the left hand, in a case where the housing portion is provided on a far side with respect to the switch button disposed at the top portion of the switch box in FIG. 2.
Figure 8:
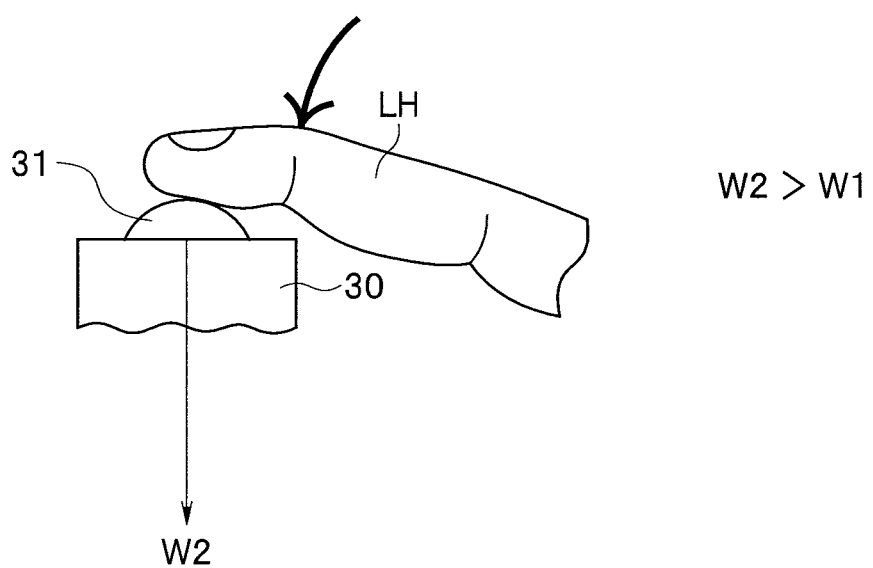
FIG. 8 schematically illustrates a situation where the operator who grasps the operation portion as illustrated in FIG. 2 depresses the switch button disposed at the top portion of the switch box in FIG. 2 with the index finger of the left hand.

FIG. 7 schematically illustrates a situation where the operator who grasps the operation portion as illustrated in FIG. 2 depresses a switch button disposed at a top portion of a switch box in FIG. 2 with the index finger of the left hand, in a case where the housing portion is provided on a far side with respect to the switch button disposed at the top portion of the switch box in FIG. 2. FIG. 8 schematically illustrates a situation where the operator who grasps the operation portion as illustrated in FIG. 2 depresses the switch button disposed at the top portion of the switch box in FIG. 2 with the index finger of the left hand.

As illustrated in FIG. 1, an endoscope 1 includes an insertion portion 2 configured to be inserted into a subject or an object, and an operation portion 6 provided on the proximal end side of the insertion portion 2 and configured to be grasped and operated by an operator.

In addition, the endoscope 1 includes a universal cord 7 extended from the operation portion 6, and a connector, not illustrated, provided at the extension end of the universal cord 7.

Note that the connector is configured to be connectable to a known light source apparatus, a known video processor, and the like, that are not illustrated, which makes the endoscope 1 connectable to peripheral apparatuses.

The insertion portion 2 includes a main part configured by including in the following order from the distal end side: a distal end portion 3 including inside thereof an image pickup unit not illustrated; a bending portion 4; and a flexible tube portion 5.

In the present embodiment, the bending portion 4 is configured by a first bending portion 4a and a second bending portion 4b. The first bending portion 4a is a specific part located on the distal end side of the bending portion 4. The second bending portion 4b is another specific part provided continuously with the proximal end in a longitudinal direction N (hereinafter, just referred to as proximal end) of the first bending portion 4a.

Although the bending portion 4 may be configured only by the first bending portion 4a, the bending portion 4 will be described below by taking the case where the bending portion 4 is configured by the first bending portion 4a and the second bending portion 4b as an example.

The operation portion 6 includes in the following order from the distal end side: a grasping region 6a and an operating element region 6c provided continuously with the proximal end of the grasping region 6a. The operation portion 6 is provided continuously with the proximal end of the flexible tube portion 5 through a known break preventer 20.

As illustrated in FIG. 2, the grasping region 6a is a region (grasping portion) configured to be grasped with the palm, and the middle finger LN, the ring finger LM, and the little finger LK of the left hand L of the operator. The grasping region 6a includes, on the distal end side thereof, a treatment instrument insertion port 25 through which a treatment instrument, not illustrated, is inserted into and extracted from a treatment instrument insertion path, not illustrated, provided in the operation portion 6 and the insertion portion 2.

In the operating element region 6c, various kinds of operating elements to be operated by the operator are provided. The various kinds of operating elements include a bending operation knobs 11, 12, a fixing knob 13, a fixing lever 14, a bending lever 40, and the like.

As illustrated in FIG. 6, the bending operation knobs 11, 12, when rotated with the thumb LO of the left hand L of the operator, for example, causes the first bending portion 4a to bend in four directions, i.e., up, down, left, and right directions through a known power transmitting mechanism 90 provided in the insertion portion 2 and the operation portion 6.

In other words, the first bending portion 4a is bent in a plurality of directions through the power transmitting mechanism 90 by the rotating operation of the bending operation knobs 11, 12.

In addition, the fixing knob 13, when rotated with the thumb LO, for example, fixes the rotation position of the bending operation knob 12. Furthermore, the fixing lever 14, when rotated with the thumb LO, for example, fixes the rotation position of the bending operation knob 11.

The bending lever 40, when rotated with the thumb LO, for example, causes an actuator 51 (see FIG. 6), which is to be described later, to be driven, and causes the second bending portion 4b to bend in at least one direction, through a power transmitting mechanism 200 including a wire 210 as a long member provided in a universal cord fixing member 80, to be described later, the operation portion 6, and the insertion portion 2.

In other words, the second bending portion 4b is bent by the driving force from the actuator 51 being transmitted to the second bending portion 4b through the power transmitting mechanism 200 by the rotating operation of the bending lever 40.

Note that the device with which the bending operation of the second bending portion 4b is performed is not limited to the above-described bending lever 40, but may be any device such as the knob, the switch buttons disposed on the operation portion 6, a foot switch connected to the endoscope 1 or a peripheral apparatus connected to the endoscope 1, or the like, as long as the device can give an instruction for driving the actuator 51.

In addition, as illustrated in FIG. 3, the bending operation knobs 11, 12, the fixing knob 13, the fixing lever 14, and the bending lever 40 are provided so as to protrude from a surface 6ca of the outer surface of the operating element region 6c to a first side A in a direction J intersecting the longitudinal direction N. The first side A is a side separated from the 6ca in the direction J.

In addition, a freeze switch button 35 for giving an instruction for stopping an image picked up by the image pickup unit, a switch button for suction operation 36, and a switch button for air/water feeding operation 37, for example, are disposed on the outer surface of the operating element region 6c so as to be located on a surface 6cc. The surface 6cc is a surface adjacent to a surface 6ca, more specifically, the surface 6cc is located on the same direction side as the surface on which the treatment instrument insertion port 25 is disposed, as illustrated in FIG. 1.

When the operation portion 6 is grasped by the operator as illustrated in FIG. 2, the freeze switch button 35, the switch button for suction operation 36, and the switch button for air/water feeding operation 37 are operated with the index finger LH or the middle finger LN.

The above-described functions of the switch buttons 35 to 37 are just one example, and it is needless to say that the functions are not limited to the above-described ones.

In addition, a switch box 30 is disposed on the outer surface of the operating element region 6c so as to be located on a surface 6cd. The surface 6cd adjoins the surface 6ca and the surface 6cc and is located on a far side separated from the insertion portion 2 in the longitudinal direction N with respect to the positions where the above-described switch buttons 35 to 37 are disposed.

A power source switch button 31 is disposed at the top portion of the switch box 30 in the longitudinal direction N. The power source switch button 31 is configured to turn on and off the power source of the endoscope 1, for example.

Furthermore, an iris switch button 32 is disposed on the switch box 30 so as to be located on a surface which is on the same side as the surface on which the switch buttons 35 to 37 are disposed. The iris switch button 32 is configured to change a photometry method, for example.

Furthermore, a release switch button 33 is disposed on the switch box 30 so as to be located on a surface opposed to the iris switch button 32. The release switch button 33 is configured to give an instruction for recording an image picked up by the image pickup unit, for example.

Note that the switch button 33 is operated with the thumb LO of the left hand L, for example, when the operation portion 6 is grasped as illustrated in FIG. 2.

The switch buttons 31, 32 are operated with the index finger LH of the left hand L, for example, when the operation portion 6 is grasped as illustrated in FIG. 2. Note that the switch button 32 may be operated with the thumb LO.

The above-described functions of the switch buttons 31 to 33 are just one example, and it is needless to say that the functions are not limited to the above-described ones.

One end side of the universal cord 7 is fixed to a surface 6cb of the outer surface of the operating element region 6c so as to protrude to a second side B opposite to the first side A in the direction J, as illustrated in FIG. 3. The surface 6cb adjoins the surface 6cc and the surface 6cd and is opposed to the surface 6ca in the direction J.

Specifically, a break preventer 7k, which is disposed on the one end side of the universal cord 7, is fixed to the universal cord fixing member 80 protruding from the surface 6cb to the second side B. With such a configuration, the one end side of the universal cord 7 is fixed to the universal cord fixing member 80 and extended in a direction S intersecting both the longitudinal direction N and the direction J.

Furthermore, the casing 50 as a housing member in which the actuator 51 is housed is disposed in the operating element region 6c, as described above. The actuator 51 is a power unit (power source) configured to drive the power transmitting mechanism 200 (see FIG. 6) for causing the second bending portion 4b to bend.

The casing 50 houses inside thereof at least a part of the actuator 51. In addition, the casing has an external dimension larger than the external dimension of the actuator 51, and has a predetermined length in the direction S, as illustrated in FIGS. 1 to 6.

The actuator 51 is configured to transmit a driving force from the operation portion 6 to the second bending portion 4b through the long member 210 configured by a wire, for example, of the power transmitting mechanism 200. The driving force is for causing the second bending portion 4b to bend in at least one direction. An example of the actuator 51 includes a motor.

As illustrated in FIG. 3, the actuator 51 is housed in the casing 50 which is disposed at the operation portion 6 so as to be located on the second side B opposite to the first side A in the direction J with respect to the center axis C of the insertion portion 2 and which is positioned so as not to stick out to the first side A with respect to the center axis C.

Specifically, the casing 50 is disposed by being positioned on the second side B so as not to stick out to the first side A in the direction J with respect to a surface F which is set to be parallel to the direction S so as to include the center axis C in the operation portion 6.

Furthermore, an outer surface 50g of the casing 50 is positioned on the second side B so as not to stick out to the first side A in the direction J with respect to the center axis C in the operation portion 6.

More specifically, the casing 50 is disposed in the universal cord fixing member 80 so as to protrude further to the second side B than the break preventer 7k of the universal cord 7. The casing 50 is extended along the direction S and arranged side by side with the break preventer 7k in the direction J, on the second side B with respect to the break preventer 7k in the direction J.

Furthermore, as illustrated in FIGS. 4 and 5, the casing 50 is disposed within a range M so as not to be located on a far side (which is the side far from the insertion portion) with respect to a position N2. The position N2 is set to a position not beyond the switch button 31 located in the operating element region 6c at a position on the side farthest from the insertion portion 2 in the longitudinal direction N.

In addition, as illustrated in FIGS. 4 and 5, the casing 50 is disposed within the range M so as not to be located on a near side (which is the side near to the insertion portion) with respect to a position N1. The position N1 is set to a position not beyond the switch button 37 which is positioned in the operating element region 6c at a position on the side nearest to the insertion portion 2 in the longitudinal direction N.

Since other configurations of the endoscope 1 is known, the descriptions thereof will be omitted.

Thus, in the present embodiment, the casing 50 in which the actuator 51 for generating the driving force for causing the second bending portion 4b to bend is housed is disposed in the operating element region 6c so as to be located on the second side B in the direction J with respect to the center axis C of the insertion portion 2. In addition, the casing 50 is positioned so as not to stick out to the first side A with respect to the center axis C.

With such a configuration, the casing 50 is disposed in the operating element region 6c, therefore the weight balance is excellent when the operator grasps the operation portion 6 with the left hand L as illustrated in FIG. 2.

In addition, when the operator performs switch operation of any one of the various switch buttons 31 to 33, and 35 to 37 with the index finger LH of the left hand L, the casing 50 does not interfere with the switch operation. In other words, the accessibility of the index finger LH to the various switch buttons 31 to 33 and 35 to 37 is improved, compared with the conventional apparatuses.

Furthermore, the casing 50 is disposed in the universal cord fixing member 80 so as to be side by side with the break preventer 7k on the second side B with respect to the break preventer 7k in the direction J.

Such a configuration enables the distance between the surface 6cb and the knobs 11, 12 can be reduced in the direction J, compared with the case where the casing 50 is provided at a position between the knobs 11, 12 and the universal cord on the surface 6ca as in the conventional apparatuses.

Such a configuration provides excellent accessibility to the knobs 11 to 13, and the levers 14 and 40 by the thumb LO which holds the break preventer 7k between itself and the index finger LH, without reducing the operability of the knobs and levers.

Furthermore, in the present embodiment, the casing 50 is disposed within the range M so as not to be located on the far side with respect to the position N2 set to the position not beyond the switch button 31 located in the operating element region 6c at the position on the side farthest from the insertion portion 2 in the longitudinal direction N.

If the casing 50 is provided in a region Q on the far side with respect to the switch button 31 in the longitudinal direction N as illustrated in FIG. 5, when the operator depresses the switch button 31 with the index finger LH in the state where the operator grasps the break preventer 7k with the thumb LO and the index finger LH, the operator had to move the index finger LH so as to go around the upper side of the casing 50 as illustrated by the two-dot-chain lines R1 in FIG. 5.

As a result, as illustrated in FIG. 7, the operator had to bend not only the first joint but also the second joint of the index finger LH in a U shape by substantially 90 degrees.

Therefore, the operator had to depress the switch button 31 with the tip of the index finger LH being substantially vertical to the switch button 31, and could not increase a depressing amount W1 of the switch button 31.

However, if the casing 50 is disposed in the range M not beyond the position N2 as in the present embodiment, the operator can cause the index finger LH to access the switch button 31 in a shortest distance, as illustrated by the two-dot-chain lines R2 in FIG. 5.

With such a configuration, the operator can depress the switch button 31 only by slightly bending the first joint of the index finger LH, as illustrated in FIG. 8.

The operator can depress the switch button, with the index finger LH being laid, a depressing amount W2 of the switch button 31 can be made larger than the depressing amount W1 in the case where the tip of the index finger LH is substantially vertical to the switch button (W2>W1).

As a result, the operator can perform the switch operation without bending the index finger LH largely, and a fatigue of the index finger LH at the time of the depression operation of the switch button 31 can be reduced.

In addition, the operator can cause the index finger LH to access the switch button 31 in the shortest distance in the state where the operator holds the break preventer 7k between the thumb LO and the index finger LH. As a result, the operator can operate the switch button 31 quickly.

Furthermore, in the present embodiment, the casing 50 is disposed within the range M so as not to be located on the near side with respect to the position N1 set to the position not beyond the switch button 37 which is positioned in the operating element region 6c at the position on the side nearest to the insertion portion 2 in the longitudinal direction N.

If the casing 50 is disposed in a region P on the near side with respect to the switch button 37 in the longitudinal direction N as illustrated in FIG. 5, when the operator grasps the grasping region 6a with the left hand L, the grasping position will be near to the insertion portion 2 side in the longitudinal direction N due to the location of the casing 50.

In such a case, if the operator depresses the switch button 37 with the index finger LH, the weight balance of the operation portion 6 becomes bad, since the casing 50 is not disposed in the operating element region 6c, and a large moment is applied to the switch box 30 side in the operating element region 6c. Furthermore, in such a case, the vicinity of the position opposed to the switch button 37 in the direction S is not grasped by the operator. Therefore, in the case where an operator with small hands grasps the operation portion 6, in particular, the operation portion 6 might be possibly unstable after the operator performs the depression operation of the switch button 37.

However, as in the present embodiment, if the casing 50 is disposed in the range M so as not to be located on the near side with respect to the position N1 set to the position not beyond the switch button 37, the weight balance of the operation portion 6 becomes excellent. In addition, the operator grasps the position in the vicinity of the position opposed to the switch button 37 in the direction S in the grasping region 6a.

Therefore, even if the operator with small hands grasps the grasping region 6a and performs the depression operation of the switch button 37, the operation portion 6 does not become unstable.

Thus, it is possible to provide the endoscope 1 having the configuration in which the casing 50 that houses the actuator 51 can be disposed at the position where the weight balance of the operation portion 6 is optimal and the casing 50 does not interfere with the operation of the switches 31 to 33 and 35 to 37 by the operator and the arrangement of the switches.

In the above-described present embodiment, the actuator 51 transmits the driving force for causing the second bending portion 4b to bend, through the power transmitting mechanism 200.

However, the present invention is not limited to the above-described configuration. It is needless to say that the present invention is applicable to the configuration in which the driving force for causing the first bending portion 4a to bend is transmitted through the power transmitting mechanism 90 by operating the knobs 11, 12, for example.

Furthermore, it is needless to say that the same effects as those of the present embodiment can be obtained even if the present invention is applied to a configuration for transmitting a driving force for electrically driving another specific part other than the second bending portion 4b provided in the insertion portion 2, i.e., a rotation body provided in the distal end portion 3, for example.

What is claimed is:

1. An endoscope comprising:
an insertion portion;
an operation portion positioned proximally relative to the insertion portion, the operation portion including a side surface;
a holder protruding from the side surface in a first direction intersecting a longitudinal direction of the operation portion;
a cord extending from the holder in a second direction intersecting each of the longitudinal direction and the first direction; and
an actuator protruding from the holder;
wherein the cord is positioned between the side surface and the actuator along the first direction; and
the actuator is provided in a casing in which at least a part of the actuator is housed and which has an external dimension larger than an external dimension of the actuator.

2. The endoscope according to claim 1, wherein
the operation portion includes a grasping region and an operating element region, the grasping region disposed on a side of the insertion portion in the longitudinal direction, the operating element region disposed on a proximal end side in the longitudinal direction of the grasping region and including a knob configured to operate a bending portion of the insertion section and one or more switch buttons, and
the actuator is provided in a housing positioned in the operating element region, the operating element region being from a proximal-most portion of the operating portion to a switch button of the one or more switch buttons furthest from the proximal-most portion.

3. The endoscope according to claim 1, wherein
the operation portion includes a grasping region and an operating element region, the grasping region being disposed on a side of the insertion portion in the longitudinal direction, the operating element region being disposed on a proximal end side in the longitudinal direction of the grasping region and including a knob configured to operate a bending portion of the insertion section and two or more switch buttons, and
the actuator is provided in a housing positioned in the operating element region, the operating element region being from a proximal-most switch button of the two or more switch buttons to a distal-most switch button of the two or more switch buttons.

4. The endoscope according to claim 1, wherein
the insertion portion comprises a first bending portion disposed on a distal end side of the insertion portion in the longitudinal direction of the insertion portion, the first bending portion being configured to bend in a plurality of directions in accordance with an operation of a knob arranged on the operation portion,
the insertion portion comprising is a second bending portion disposed continuously with the first bending portion, and
the actuator is configured to transmit a driving force from the operation portion to the second bending portion through a long member for bending the second bending portion in at least one direction.

5. The endoscope according to claim 1, wherein the actuator extends from the holder in the second direction.

6. The endoscope according to claim 1, wherein the side surface is a first side surface; and
the endoscope further comprises a knob configured to operate a specific part of the insertion portion, the knob protruding from the operation portion from a second side surface of the operation portion.

7. The endoscope according to claim 6, wherein the cord is positioned between the actuator and the knob along the first direction.

8. The endoscope according to claim 6, wherein the specific part is a bending portion of the insertion section.

9. The endoscope according to claim 6, wherein the second side surface opposes the first side surface across a longitudinal axis.

10. The endoscope according to claim 1, wherein
the side surface comprises a first side surface;
the operation portion includes a lever positioned on a second side surface of the operation portion, the lever configured to operate an actuator; and
the actuator is positioned on the first side surface, the first side surface being opposite to the second side surface across the longitudinal axis.

11. The endoscope according to claim 1, wherein the lever is configured to move in the second direction.

12. The endoscope according to claim 1, wherein the operation portion includes a gear having an axis of rotation intersecting a longitudinal direction of the operation portion, the gear configured to transmit a rotation power of the actuator to a part of the insertion portion.

13. The endoscope according to claim 12, wherein the axis of rotation intersects the second direction.

14. The endoscope according to claim 1, wherein the actuator protrudes from the holder in the second direction.

15. The endoscope according to claim 14, wherein the cord extends parallel to the actuator.

16. The endoscope according to claim 1, wherein a bottom surface of the actuator is positioned between a top surface of the actuator and a bottom surface of the cord along the longitudinal direction.

17. An endoscope comprising:
an insertion portion;
an operation portion positioned proximally relative to the insertion portion, the operation portion including a side surface;
a holder protruding from the side surface in a first direction intersecting a longitudinal direction of the operation portion;
a cord extending from the holder in a second direction intersecting each of the longitudinal direction and the first direction; and
an actuator protruding from the holder;
wherein the cord is positioned between the side surface and the actuator along the first direction;
the side surface is a first side surface; and
the endoscope further comprises a knob configured to operate a specific part of the insertion portion, the knob protruding from the operation portion from a second side surface of the operation portion.

18. An endoscope comprising:
an insertion portion;
an operation portion positioned proximally relative to the insertion portion, the operation portion including a side surface;

a holder protruding from the side surface in a first direction intersecting a longitudinal direction of the operation portion;
a cord extending from the holder in a second direction intersecting each of the longitudinal direction and the first direction; and
an actuator protruding from the holder;
wherein the cord is positioned between the side surface and the actuator along the first direction;
the side surface comprises a first side surface;
the operation portion includes a lever positioned on a second side surface of the operation portion, the lever configured to operate an actuator; and
the actuator is positioned on the first side surface, the first side surface being opposite to the second side surface across the longitudinal axis.

* * * * *